US008655798B2

(12) United States Patent
Humphrey et al.

(10) Patent No.: US 8,655,798 B2
(45) Date of Patent: Feb. 18, 2014

(54) BLOOD FLOW BYPASS CATHETERS AND METHODS FOR THE DELIVERY OF MEDIUM TO THE VASCULATURE AND BODY DUCTS

(75) Inventors: Joseph A. C. Humphrey, Charlottesville, VA (US); George T. Gillies, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 13/559,008

(22) Filed: Jul. 26, 2012

(65) Prior Publication Data

US 2013/0085386 A1    Apr. 4, 2013

Related U.S. Application Data

(60) Continuation of application No. 12/625,153, filed on Nov. 24, 2009, now Pat. No. 8,255,193, which is a division of application No. 11/884,421, filed as application No. PCT/US2006/005876 on Feb. 16, 2006, now abandoned.

(60) Provisional application No. 60/653,397, filed on Feb. 16, 2005.

(51) Int. Cl.
 *G06G 7/50* (2006.01)
 *G06F 19/00* (2011.01)
 *A61M 25/00* (2006.01)
 *A61B 5/0215* (2006.01)

(52) U.S. Cl.
 USPC ............ 706/6; 703/1; 703/2; 703/11; 702/19; 427/2.25; 600/433; 600/434; 600/435; 600/585

(58) Field of Classification Search
 None
 See application file for complete search history.

(56) References Cited

U.S. PATENT DOCUMENTS

| | | | |
|---|---|---|---|
| 4,423,725 A | 1/1984 | Baran |
| 5,021,044 A | 6/1991 | Sharkawy |
| 5,254,089 A | 10/1993 | Wang |
| 5,390,283 A | 2/1995 | Eshelman |
| 5,716,340 A | 2/1998 | Schweich |
| 5,792,105 A | 8/1998 | Lin et al. |
| 5,840,066 A | 11/1998 | Matsuda et al. |
| 5,868,778 A | 2/1999 | Gershony |
| 6,012,034 A | 1/2000 | Hamparian |
| 6,139,517 A | 10/2000 | Macoviak |
| 6,173,286 B1 | 1/2001 | Guttman |
| 6,285,968 B1 | 9/2001 | Motoyama et al. |
| 6,506,180 B1 | 1/2003 | Lary |
| 6,533,767 B2 | 3/2003 | Johansson |
| 6,533,800 B1 | 3/2003 | Barbut |
| 6,558,356 B2 | 5/2003 | Barbut |
| 6,558,401 B1 | 5/2003 | Azizi |
| 6,565,552 B1 | 5/2003 | Barbut |
| 6,582,448 B1 | 6/2003 | Boyle |
| 6,592,557 B2 | 7/2003 | Barbut |
| 6,613,076 B1 | 9/2003 | Cherif-Cheikh |
| 6,627,900 B2 | 9/2003 | Fukui |
| 6,635,046 B1 | 10/2003 | Barbut |
| 6,660,021 B1 | 12/2003 | Palmer |
| 6,663,613 B1 | 12/2003 | Evans |
| 6,676,650 B1 | 1/2004 | Magovern et al. |
| 6,712,798 B2 | 3/2004 | Constantz |
| 6,712,806 B2 | 3/2004 | St. Germain |
| 6,730,063 B2 | 5/2004 | Delaney |
| 6,733,474 B2 | 5/2004 | Kusleika |
| 6,743,196 B2 | 6/2004 | Barbut |
| 6,743,208 B1 | 6/2004 | Coyle |
| 6,755,846 B1 | 6/2004 | Yadav |
| 6,767,345 B2 | 7/2004 | St. Germain |
| 6,790,204 B2 | 9/2004 | Zadno-Azizi |
| 6,796,992 B2 | 9/2004 | Barbut |
| 6,830,577 B2 | 12/2004 | Nash |
| 6,830,579 B2 | 12/2004 | Barbut |
| 6,840,949 B2 | 1/2005 | Barbut |
| 7,831,418 B1 | 11/2010 | Sendhoff et al. |
| 8,255,193 B2 | 8/2012 | Humphrey et al. |
| 2001/0023325 A1 | 9/2001 | Ferrera |
| 2003/0014191 A1 | 1/2003 | Agrafiotis |

(Continued)

FOREIGN PATENT DOCUMENTS

EP    1186747    3/2002
WO    WO 2006/015091    2/2006

OTHER PUBLICATIONS

Baker, J. E. "Reducing Bias and Inefficiency in the Selection Algorithm." Proceedings of the Second International Conference on Genetic Algorithms, L. Eribaum Associates, 1987, p. 14-21, Hillsdale, NJ.

Cannan, C. R. "Novel Perfusion Sleeve for Use During Balloon Angioplasty: Initial Clinical Experience." Catheterization and Cardiovascular Diagnosis, 1998, vol. 44, p. 358-362.

Cho, K. J. "Pattern of Dispersion from a Pulse-Spray Catheter for Delivery of Thrombolytic Agents: Design, Theory, and Results." Academic Radiology, 1997, vol. 4, p. 210-216.

Cokelet, G. R. "The Rheology and Tube Flow of Blood." Skalak, R. And Chien, S. (editors), Handbook of Bioengineering, McGraw-Hill Book Company, Chapter 14, 1987, p. 14.1-14.17, New York.

(Continued)

*Primary Examiner* — Lori A Clow
(74) *Attorney, Agent, or Firm* — Robert J. Decker; Kilpatrick Townsend & Stockton LLP

(57) ABSTRACT

A catheterization device that may be designed by use of an adaptive genetic algorithm computational fluid dynamics approach, as well as other Global Optimization methods that may include simulated annealing, multistart and interval methods, continuous branch and bound methods, evolutionary algorithms, and tabu search and scatter search methods, as well as other available Global Optimization methods that is able to maximize/optimize the dwell time of an infused agent in the vicinity of a vascular lesion. The device may have an internal by-pass channel that allows the blood upstream of the lesion to continue its pulsatile flow through the vessel in the part of it occluded by the lesion, while simultaneously allowing the disbursement and maximal dwell time of an anti-thrombolytic or other diagnostic or therapeutic agent needed to treat the lesion.

19 Claims, 8 Drawing Sheets

(56) References Cited

U.S. PATENT DOCUMENTS

| | | |
|---|---|---|
| 2003/0034918 A1 | 2/2003 | Werner |
| 2003/0216710 A1 | 11/2003 | Hurt |
| 2004/0162519 A1 | 8/2004 | Helkowski |
| 2005/0107845 A1 | 5/2005 | Wakefield |
| 2005/0117165 A1 | 6/2005 | Holbrook |
| 2005/0199555 A1 | 9/2005 | Pollock |
| 2006/0025752 A1 | 2/2006 | Broaddus |

OTHER PUBLICATIONS

Davis, L. (editor). "What is a Genetic Algorithm?" Handbook of Genetic Algorithms, Van Nostrand Reinhold, Chapter 1, 1991, p. 1-22, New York.

Enderle, J., Blanchard, S., and Bronzino, Jr. (editors). "Cardiovascular Mechanics." Introduction to Biomedical Engineering, Academic Press, Chapter 10, 2000, p. 467-536, New York.

Grefenstette, J. J. "Optimization of Control Parameters for Genetic Algorithms." IEEE Transactions on Systems, Man, and Cybernetics 1986, vol. SMC-16, No. 1, p. 122-128.

Holland, J. H. "Adaptation in Natural and Artificial Systems." The University of Michigan Press, 1975, p. 1-19.

Kaplan, A. V. "Heparin Delivery at the Site of Angioplasty with a Novel Drug Delivery Sleeve." The American Journal of Cardiology, 1996, vol. 77, p. 307-310.

Moura, A. "Intramural Delivery of Agent via a Novel Drug-Delivery Sleeve: Histological and Functional Evaluation." American Heart Association Circulation, 1995, vol. 92, No. 8, p. 2299-2305.

Queipo, N. V. "Multiobjective Optimal Placement of Convectively Cooled Electronic Components on Printed Wiring Boards." IEEE Transactions on Components, Packaging, and Manufacturing Technology, 1988, Part A, vol. 21, No. 1, p. 142-153.

Queipo, N. "Genetic Algorithms for Thermosciences Resarch: Application to the Optimized Cooling of Electronic Components." International Journal of Heat and Mass Transfer, vol. 37, No. 6, 1994, p. 893-908.

Yang, X. "Imaging of Vascular Gene Therapy." Radiology, 2003, vol. 228, No. 1, p. 36-49.

Mareels et al (Artificial Organs, 28(7):639-648, 2004).

Abramson et al (SC2001 Nov. 2001, ACM, p. 1-12).

Parry et al. (IEEE Transactions on Components and Packaging Technologies, vol. 27, No. 2, p. 391-397, Jun. 2004).

Kuzmin ("Introduction to computational fluid dynamics", 2004, Available on the internet at [http://web.archive.org/web/20040907093749/http://www.mathematik.uni-dortmund.de/-kuzmin/cfdintro/lecture1.pdf]).

Markou et al. (Annals of Biomedical Engineering, vol. 26, pp. 502-511, 1998).

Grigioni et al. (Journal of Biomechanics, vol. 35, p. 1599-1612, 2002).

Poloni et al. (Comput. Methods Appl. Mech. Engrg., vol. 186, p. 403-420, 2000).

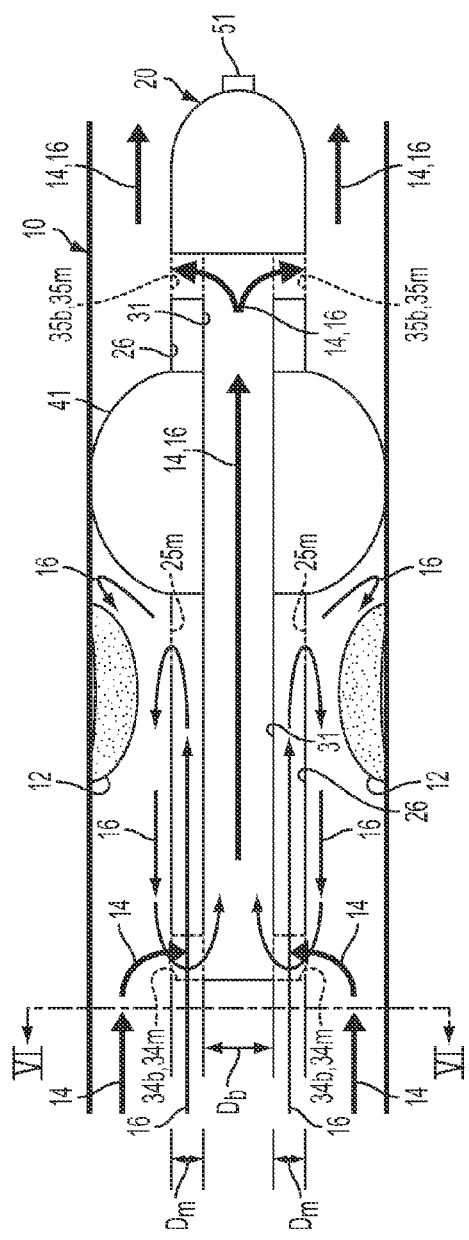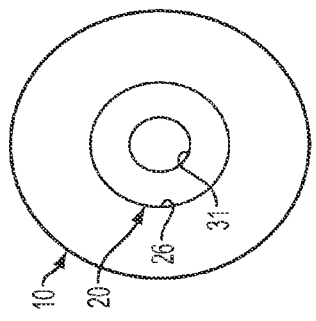

BLOOD FLOW BYPASS CATHETERS AND METHODS FOR THE DELIVERY OF MEDIUM TO THE VASCULATURE AND BODY DUCTS

CROSS-REFERENCES TO RELATED APPLICATIONS

This application is a continuation of U.S. application Ser. No. 12/625,153 filed on Nov. 24, 2009 now U.S. Pat. No. 8,255,193, which is a divisional of U.S. application Ser. No. 11/884,421 filed on Aug. 15, 2007 now abandoned, which is a National Stage filing of International Application No. PCT/US2006/005876 filed on Feb. 16, 2006, which claims priority under 35 USC §119 from U.S. Provisional Patent Application Ser. No. 60/653,397 filed on Feb. 16, 2005, entitled "Blood Flow Bypass Catheter for the Delivery of Agents to Lesions in the Peripheral Vasculature," the contents of all of which are hereby incorporated herein by reference in their entireties for all purposes.

FIELD OF THE INVENTION

The invention relates to the field of catheterization devices and methods for delivering a medication or the like to a lesion in a vascular structure or duct of a patient, as well as a method of for generating configuration catheterization device designs for optimizing performance.

BACKGROUND OF THE INVENTION

The need for developing ever more efficacious methods of treating peripheral vascular disease (PVD) which, like coronary artery disease (CAD), is the progressive narrowing of the arterial tree by the atherosclerotic process. These diseases result in diminished blood flow to vital organs and extremities beyond the site of narrowing or occlusion: Diabetes mellitus (DM) is a major contributor to such disease processes, as are a large number of other well-known health risks and factors, such as elevated levels of cholesterol. As the prevalence of these factors increases, so does that of PVD and CAD. For example, PVD affects an estimated 27 million people in Europe and North America, and it produces significant morbidity and mortality in those populations. An estimated 10.5 million of those affected are symptomatic while 16.5 million are asymptomatic. Despite the prevalence of PVD, it is estimated that only 25% of symptomatic patients are currently treated for the disease.

PVD typically affects multiple segments of a given artery. Short segments of severe narrowing are typically treated with catheter-based techniques such as angioplasty and the placement of one or more stents. When there is severe narrowing over a long segment or involving multiple arteries within a limb, surgical revascularization is the treatment of choice. When this is insufficient, particularly in the diabetic population, limb amputation is indicated, and an estimated 60,000 are performed annually in the United States. Severe narrowing within the vessel or related causes of poor blood flow commonly result in the formation of intra-arterial thrombus (clot) formation, which, if not immediately corrected, will lead to the death of tissue and the need for amputation of the host limb. Endovascular catheter placement for the delivery of a thrombolytic agent to dissolve the clot is efficacious, but commonly requires days of drug infusion, intensive care monitoring, and frequent trips to a radiology suite to reposition the catheter.

Systemic administration of therapeutic agents allows for wide-spread distribution of these agents throughout the body. The function of the therapeutic agent depends upon the uptake of the medication by the targeted organ and upon the agent's pharmacokinetics which determine its concentration as a function of time. However, with systemic delivery, non-targeted organs may be adversely affected by the medication, and this can cause potentially serious side-effects. Consequently, the efficacy of the therapeutic agents at the target site can be limited by both its concentration at the site of interest and by its toxicity in other non-targeted organs.

The clinical benefits of site-specific catheter-based delivery systems for the administration of therapeutics can include increased safety, increased efficacy, reduced toxicities, more reliable therapeutic drug levels, and decreased and simplified dosing requirements. Safety, efficacy and toxicity are all independent but related parameters in the pharmacokinetics of each therapeutic agent. Site-specific drug delivery into the target tissue ensures that the majority of the drug goes to the site it is intended to act upon with minimal or at least small and tolerable effect upon non-targeted tissue, thereby decreasing the effects of toxicity. This allows for higher concentrations of the therapeutic agent to be administered to the targeted site, thereby increasing the efficacy of the agent. An additional benefit of site-specific delivery of therapeutic agents is that the patient receives a smaller cumulative dose, thereby further reducing the overall risk to the patient.

Site-specific catheter-based drug delivery allows local administration of therapeutic agents and reliable therapeutic drug levels to be achieved and maintained because systemic clearance is reduced By obtaining reliable therapeutic drug levels in this manner, dosing requirements are decreased and simplified. As mentioned above, local drug levels can be maintained at higher levels than could be achieved with systemic administration because systemic toxicity is reduced with local delivery.

A site-specific drug-delivery catheter is also required when active biologic agents are being administered to a focal site of injury. As an example, site-specific delivery of thrombolytic therapy to the site of a clot in the vascular tree of an ischemic limb is preferred to systemic delivery. With site-specific delivery, a high local concentration of the thrombolytic agent can be delivered to achieve lysis of the clot material at the site of infusion, whereas, systemic delivery of a thrombolytic therapy could lead to generalized bleeding at multiple remote sites.

An emerging modality for the treatment of PVD is site-specific stem cell therapy for the treatment of ischemic limbs. This cellular therapy has demonstrated efficacy in the formation of new blood vessels in ischemic limbs of patients with PVD in a recently published randomized controlled clinical study. The increasing population of patients with DM and PVD potentially makes this a very large market.

One alternative that can obviate the problem of washout of the thrombolytic agent downstream from the lesion is to occlude the artery with a blockage means such as a balloon placed distally from the lesion being treated. While effective over brief periods intra-operatively, this approach does limit the time over which the agent can act, because downstream arterial occlusion cannot be maintained indefinitely without ischemic injury to dependent tissues and organs. These problems arise not only with the catheter-based delivery of thrombolytics, but also when delivering new and emerging classes of agents such as stem cell suspensions and angiogenesis factors.

These clinical needs have driven many substantial efforts aimed at catheter development over the past several years, and a variety of devices has been designed as a result. Generally speaking, the most interesting class of devices is that which incorporates internal channels or create pathways that allow blood flow past the lesion while drugs or other therapies are being delivered to the lesion either through a balloon that is integral to the catheter or from ports elsewhere on it. Integral balloons can also be used to carry out angioplasty on the lesion or to temporarily block the artery during drug delivery to the lesion. Within the medical device community, such catheters are often referred to as perfusion sleeves, and there is a large literature on the topic. For a succinct overview of the spectrum of catheters that includes some of these devices see Yang (Yang X imaging of Vascular Gene Therapy. *Radiol.* 228:36-49, 2003, of which is hereby incorporated by reference herein in its entirety) who lists several of the commercially available systems now being employed for the image-based delivery of intravascular gene therapies.

A frequent use of perfusion sleeve devices is within the context of percutaneous transluminal angioplasty, although applications for them in a variety of other interventions have been conceived, clinically tested, and put into routine use as well. An early multiple-cuff catheter with windows on the shaft to shunt the arterial blood flow past the treatment zone was described by Baran et al. (Baran O E, Baran A O D: Multiple Surgical Cuff. U.S. Pat. No. 4,423,725, 1984, of which is hereby incorporated by reference herein in its entirety). Others are those of Schweich et al. (Schweich Jr. C J, Harrison K D, Burns M M: Blood Perfusion Catheter. U.S. Pat. No. 5,716,340, 1998, of which is hereby incorporated by reference herein in its entirety), who introduced a perfusion-shunt channel via an inflatable balloon wound toroidally around the catheter shaft, and Macoviak et al. (Macoviak J A, Samson W J, Leary J J, Esch B D: Perfusion Shunt Apparatus and Method, U.S. Pat. No. 6,239,517, 2000, of which is hereby incorporated by reference herein in its entirety), who developed a stand-alone shunt apparatus that could be mounted on a catheter for use in the aortic arch. Lary (Lary B G: Passive Perfusion Sleeve/Placement Catheter Assembly. U.S. Pat. No. 6,506,180, 2003, of which is hereby incorporated by reference herein in its entirety) incorporated a specially designed inflation lumen for the perfusion sleeve's angioplasty balloon.

Several types of perfusion sleeve devices have also been designed for drug delivery simultaneous with balloon angioplasty. One such catheter described in the literature for this purpose was the "infusion sleeve" system of Moura et al. (Moura A, Jules Y T, Lam M D, Hébert D, Kermode J R, Grant O W, Robitaille D, Klein E J, Yock P G, Simpson J B, Kaplan A V: Intramural Delivery of Agent via a Novel Drug-Delivery Sleeve, *Circulation* 92:2299-2305, 1995, of which is hereby incorporated by reference herein in its entirety), which was used for applications such as the delivery of heparin to lesions on the arterial wall (Kaplan A V, Vandormael M, Hofmann M, Weil H J, Störger H, Krajcar M. Gallant P. Simpson J B, Reifart N: Heparin Delivery at the Site of Angioplasty with a Novel Drug Delivery Sleeve. *Am. J. Cardiol.* 77:307-310, 1996, of which is hereby incorporated by reference herein in its entirety). A variant of it that was optimized specifically for perfusion capabilities was introduced in 1998 (Cannan C R, Kaplan V A, Klein E S, Galant P, Sharaf B L, Williams D O: Novel Perfusion Sleeve for Use During Balloon Angioplasty: Initial Clinical Experience. *Cathateriz Cardiovasc. Diag.* 44:358-362, 1998, of which is hereby incorporated by reference herein in its entirety) and subsequently used in angioplasty procedures. Examples of some other more recent flow bypass devices include those described by Evans at al. (Evans M A, Demarais D M, Eversull C S, Leeflang S A: System and Methods for Clot Dissolution, U.S. Pat. No. 6,663,613, 2003, of which is hereby incorporated by reference herein in its entirety) and Zadno-Azizi et al. (Zadno-Azizi G R, Patel M R, Muni K P, Bagaosian C J, Ha H V: Method for Containing and Removing Occlusions in the Carotid Arteries. U.S. Pat. No. 6,90,204, 2004, of which is hereby incorporated by reference herein in its entirety).

A general and consistent limitation of the prior art is that, among other things, the bulk of the design work on this class of catheters has been done without detailed assessment of the flows by reference to Computational Fluid Dynamics (CFD) or to experiments performed on scaled up physical platforms that retain geometrical and dynamical similarity with the catheters. Instead, much of the modeling has been far more empirical in nature, relying typically on observations with prototype devices, and with the design iterations then made largely on the basis of those results. This is a perfectly valid approach and has been used, for example, to investigate side-slit versus side-hole geometries for drug delivery ports on intravascular pulse-spray catheters (Cho K J, Recinella D K: Pattern of Dispersion from a Pulse-Spray Catheter for Delivery of Thrombolytic Agents. Acad. Radiol. 4:210-216, 1997, of which is hereby incorporated by reference herein in its entirety). On the other hand, the total cross-sectional area of a 3 mm inner-diameter artery is only 7 $mm^2$, thus restricting the catheter cross section to perhaps 5 $mm^2$ or less, for such an artery. Therefore, the real estate available for a balloon inflation lumen, a drug delivery lumen, a perfusion bypass lumen, a guidewire channel, etc. is very limited. As a result, biomedical engineers have often had to introduce complex multi-purpose channels into their catheter designs in order to circumvent this limitation.

SUMMARY OF THE INVENTION

To overcome this general limitation, we set forth herein a design process for perfusion sleeve catheters based on, among other things, the combination of adaptively guided computational fluid dynamics (CFD) modeling and scaled up experiments of the flows and species mass transport involved that can provide useful quantitative guidance on the geometry and relative placement of port holes, internal lumens and other structural features of the catheter that critically impact its performance. In particular, we provide an adaptive design process based on a Genetic Algorithm-guided CFD approach (or other global optimization-guided approaches; as well as any other suitable and available approaches/algorithms) that leads to non-intuitively designed catheters that allow for indefinitely long dwell time of a thrombolytic agent (or other optimizations of concentration levels and time) in the vicinity of a lesion while maximizing the blood flow (or other optimizations of concentration levels and time) bypassed around the lesion.

Therefore, according to various embodiments of the present invention, catheter designs are provided for which the blood flow through the region of the lesion can continue uninterrupted while the medication is being simultaneously applied to the lesion such that the treatment concentration levels and time are optimized.

Further, methods (e.g., techniques and algorithms) for positioning and utilizing the catheter are provided for optimizing the concentration and dwell time of the medication being applied to the lesion.

An aspect of various embodiments of the present invention, provides a catheter device for insertion into a vascular structure or body duct, wherein the catheter device is designed by employment of a global optimization algorithm based computational fluid dynamics approach. The catheter device having a distal end and a proximal end for delivery of a medium to a lesion. The device comprising: a blood lumen for allowing blood to pass there through; a medium lumen for the delivery of a medium to the lesion, the medium lumen comprising at least one medium egress port for communication with the lesion; an expandable component disposed on the catheter device to block or impede the vascular flow of blood in the vascular structure or body duct; and the blood lumen comprising at least one blood entrance port proximally before the expandable component to allow blood to enter and at least one blood egress port distally beyond the expandable component to allow blood to pass distally beyond the expandable component. The global optimization algorithm may comprise a genetic algorithm/method. The global optimization algorithm may comprise at least one of: simulated annealing, multistart and interval methods, continuous branch and bound methods, evolutionary algorithms, and tabu search and scatter search methods, as well as other available Global Optimization methods. Furthermore, any other suitable and available approach/algorithm may be implemented as well.

An aspect of various embodiments of the present invention provides for a method for delivering a medium to a lesion inside of a vascular structure or body duct by inserting a catheter device designed by a global optimization algorithm based computational fluid dynamics approach into a subject. The catheter device having a distal end and a proximal end, lumens there through, medium port holes, and blood port holes. The method comprises; inflating an expandable component to block or impede the vascular flow of blood or other body fluid through the vasculature structure or the body duct; delivering the medium through one of the lumens to the lesion through at least one of the medium port holes; and allowing blood of the vasculature of the subject to proximally enter through at least one of the blood port holes and flow through one of the lumens and to exit on a side of the lesion toward the distal end of the catheter device through at least one of the blood port holes. The global optimization algorithm may comprise a genetic algorithm/method. The global optimization algorithm may comprise at least one of simulated annealing, multistart and interval methods, continuous branch and bound methods, evolutionary algorithms, and tabu search and scatter search methods, as well as other available Global Optimization methods. Furthermore, any other suitable and available approach/algorithm may be implemented as well.

An aspect of various embodiments of the present invention provides for a method for generating a configuration of elements of a catheter device for use inside a vasculature or body duct of a subject that includes inserting the catheter device into the subject. The catheter device comprising passages for blood flow and medium flow and inlet and exit ports for blood flow and medium flow. The method comprising: selecting variables including at least one of: a) geometrical shapes and dimensions of at least some of the blood passages and the medium passages, and b) relative locations and orientations of now panes of at least some of the inlet ports and exit ports; and applying a global optimization algorithm to the variables to generate a catheter with optimized flow conditions. The global optimization algorithm may comprise a genetic algorithm/method. The global optimization algorithm may comprise at least one of simulated annealing, multistart and interval methods, continuous branch and bound methods, evolutionary algorithms, and tabu search and scatter search methods, as well as other available Global Optimization methods. Furthermore, any other suitable and available approach/algorithm may be implemented as well.

An aspect of various embodiments of the present invention provides for a computer program product comprising a computer useable medium having computer program logic for enabling at least one processor in a computer system to generate a configuration of elements on a catheter device. The catheter device intended may be intended for use inside a vasculature or body duct of a subject that includes inserting the catheter device into the subject. The catheter device comprising passages for blood flow and medium flow and inlet and exit ports for blood flow and medium flow. The computer program logic comprising: selecting variables including at least one of: a) geometrical shapes and dimensions of at least some of the blood passages and the medium passages, and b) relative locations and orientations of flow planes of at least some of the inlet ports and exit ports; and applying a global optimization algorithm to the variables to generate a catheter with optimized flow conditions. The global optimization algorithm may comprise a genetic algorithm/method. The global optimization algorithm may comprise at least one of simulated annealing, multistart and interval methods, continuous branch and bound methods, evolutionary algorithms, and tabu search and scatter search methods, as well as other available Global Optimization methods. Furthermore, any other suitable and available approach/algorithm may be implemented as well.

An aspect of various embodiments of the present invention provides for a catheter device for insertion into a vascular structure or body duct, wherein the catheter device includes a distal end and a proximal end for delivery of a medium to a lesion, The device comprising: a blood lumen for allowing blood to pass there through; a medium lumen for the delivery of a medium to the lesion, the medium lumen comprising at least one medium egress port for communication with the lesion; an expandable component disposed on the catheter device to block or impede the vascular flow of blood in the vascular structure or body duct; and the blood lumen comprising at least one blood entrance port proximally before the expandable component to allow blood to enter and at least one blood egress port distally beyond the expandable component to allow blood to pass distally beyond the expandable component. The medium may include, for example and not limited thereto, at least one of the following: agent, substance, material, fluid, gas/air, thrombolytic agents, clot lysis agents, chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic agent and/or diagnostic agent.

An aspect of various embodiments of the present invention provides a method for delivering a medium to a lesion inside of a vascular structure or body duct by inserting a catheter device into a subject. The catheter device may have a distal end and a proximal end, lumens there through, medium port holes, and blood port holes. The method comprises: inflating an expandable component to block or impede the vascular flow of blood or other body fluid through the vasculature structure or the body duct; delivering the medium through one of the lumens to the lesion through at least one of the medium port holes; and allowing blood of the vasculature of the subject to proximally enter through at least one of the blood port holes and flow through one of the lumens and to exit on a side of the lesion toward the distal end of the catheter device through at least one of the blood port holes. The medium may include, for example and not limited thereto, at least one of the following: agent, substance, material, fluid, gas/air, thrombolytic agents, clot lysis agents, chemotherapies, cell slurries, gene therapy vectors, growth factors, contrast ager angiogenesis factors, radionuclide slurries, anti-infection agents, anti-tumor compounds, receptor-bound agents and/or other types of drugs, therapeutic agent and/or diagnostic agent.

An aspect of various embodiments of the present invention provides a catheterization device that may be designed by use of an adaptive genetic algorithm computational fluid dynamics approach, as well as other Global Optimization methods that may include simulated annealing, multistart and interval methods, continuous branch and bound methods, evolutionary algorithms, and tabu search and scatter search methods, as well as other available algorithms/methods that is able to, for example, maximize/optimize the dwell time of an infused agent in the vicinity of a vascular lesion. The device may have an internal by-pass channel that allows the blood upstream of the lesion to continue its pulsatile flow through the vessel in the part of it occluded by the lesion, while simultaneously allowing the disbursement and maximal dwell time of an antithrombolytic or other diagnostic or therapeutic agent needed to treat the lesion. Different embodiments of the catheterization device are disclosed and indications for the use of these devices in the treatment of vascular diseases are discussed.

The invention itself, together with further objects and attendant advantages, will best be understood by reference to the following detailed description taken in conjunction with the accompanying drawings.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIGS. 1 and 2 are cross-sectional side views of the catheter design of the present invention located within the lumen of a blood vessel where blood flow is occluded distal (or partially distal) to the lesion, and showing blood flow and delivery of an agent through the catheter.

FIG. 6 schematically illustrates a sectional view VI-VI of an embodiment of the blood flow by-pass catheter provided in FIG. 1.

DETAILED DESCRIPTION OF THE DRAWINGS

Figure 2:
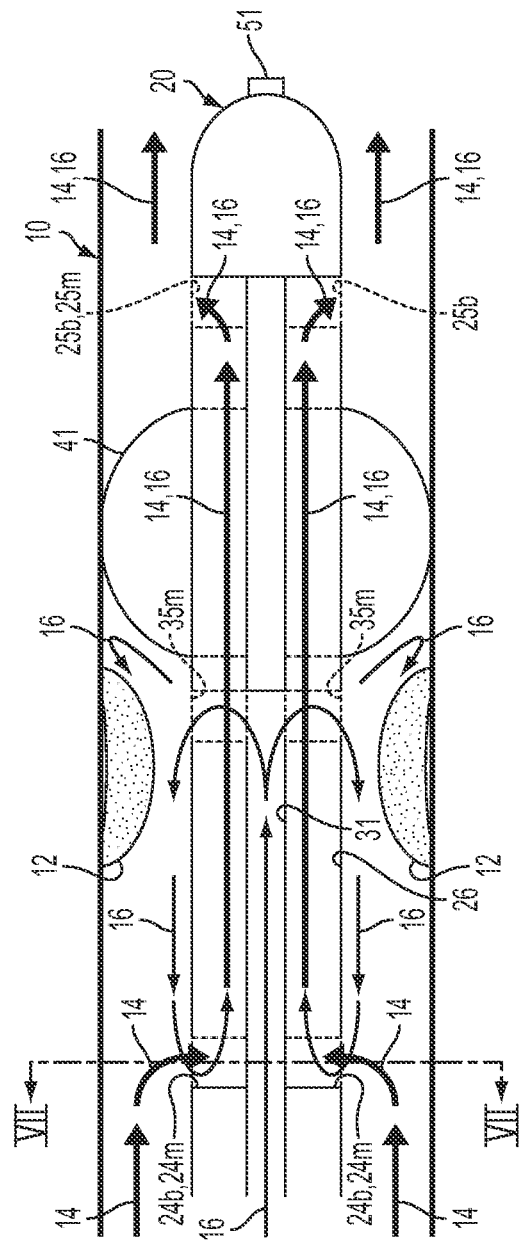

Turning now to the drawings, FIG. 1 shows one possible embodiment of a blood flow by-pass catheter 20 for irrigating thrombi or lesions in a blood vessel 10 with medium, such as medication or other diagnostic or therapeutic agent 16, or other applicable agent, substance, material medium or fluid as desired or required. Some examples of medium that may be transferred from the catheter 20 to the subject may include, but not limited thereto, the following: agent, substance, material, therapeutic and diagnostic agents, for example, thrombolytic agents, clot lysis agents, chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic and/or diagnostic agents, and other such substances. The flow of blood 14 is blocked by a temporarily enlarged portion or expandable component 41 that may be in direct or indirect communication of the outer lumen 26 (or passage) of the catheter 20 downstream (or at least partially downstream) of the thrombus or lesion 12. This forces the blood 14 through port holes 34b, for blood entrance, leading through the port hole to the inner lumen 31 (or passage), acting as the blood lumen, of the catheter 20 through which it flows until it emerges from port holes 35b, for blood egress, back into the unobstructed blood vessel 10 downstream of the blockage. The medium 16, such as medication or other diagnostic or therapeutic agent flows through an annular passage, acting as the agent or medium lumen, in the outer lumen 26 of the catheter 20 and, because the end of this passage is sealed at the blockage location, it emerges out of the outer lumen 26 through port holes 25m, for agent egress, near the thrombus or lesion 12. The presence of the blockage forces the medium or medication to re-circulate in the vicinity of the thrombus or lesion 12, thus permeating it completely. The rate of irrigation is controlled by the pressure imposed on the medium or medicated flow and is essentially independent of the blood flow rate. For example, the performance of the catheter as determined by the flow and species transport through it shall depend on, among other things, its geometrical and dynamical characteristics. The flow of medium, medication or other diagnostic or therapeutic agent 16 merges with the flow of blood 14 where it travels through the portholes 34m and enters the inner lumen 31, acting as the blood lumen, and is discharged with the blood downstream of the blockage.

Still referring to FIG. 1, a microcoil device 51 (or any other suitable imaging/tracking/guiding device or method available), as generically shown, may be located at the tip of outer catheter 20 (or specified/desired location) to help enable a high contrast magnetic resonance imaging of the catheter and its environs or a magnetic resonance spectroscopy measurement (or any other available imaging/tracking/guiding methods, procedures, techniques or treatments available) of species proximal to the tip of catheter 20 in a blood vessel, body duct, brain or other locations of a patient or subject. A more detailed discussion of the imaging/tracking/guiding device and method will be presented in regard to FIG. 8. A plurality of the microcoil devices may be used on any combination of overall catheter systems (for example, see teaching described in commonly assigned International Patent Application Serial No.: PCT/US2005/026738, to Gillies et al, filed Jul. 28, 2005, entitled "Coaxial Catheter Systems for Transference of Medium" and corresponding U.S. application Ser. No. 11/191,676, filed Jul. 28, 2005, of Which are hereby incorporated by reference herein in their entirety) to best accomplish the magnetic resonance imaging or spectroscopy.

It should be appreciated, that as discussed herein a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog or pig), etc. It should be appreciated that the subject may be any applicable patient, for example.

Moreover, it should be appreciated that the various components of the catheter device 20 as discussed herein may be a variety of commercially available materials used for all types of catheter systems. Some examples of materials used for the inner and outer catheters may include, but not limited thereto, the following: polymers, rubber, plastic, composites, metals, ceramics, hydrogels, dialysis membranes and other membranous materials, MR-compatible alloys and materials, and other organic and inorganic compounds and substances and the like. It should be appreciated that the various components of the catheter device 20, including but not limited thereto, the inner and outer lumens and components thereof; may be flexible or rigid and combination thereof as required or desired for intended use. Similarly, the catheter device 20, including but not limited thereto, the inner and outer lumens and components thereof, may provide volume contoured delivery/withdrawal (i.e., transfer) of a medium or blood by adjusting its geometry and flexibility/rigidity according to the target location or anatomy (or region, including structure and morphology of any lesion) being treated.

FIG. 2 shows another possible embodiment of a blood flow by-pass catheter 20 for irrigating thrombi or lesions in a blood vessel 10 with a medium, such as a medication or other diagnostic or therapeutic agent 16, or other applicable medium or fluid as desired or required. The flow of blood 14 is blocked by a temporarily enlarged portion or expandable component 41 that may be in direct or indirect communication of the outer lumen (or passage) 26 of the catheter 20 downstream (or at least partially downstream) of the thrombus or lesion 12. This forces the blood 14 through port holes 24*b*, for blood entrance, leading to the outer lumen (passage or annulus) 26, acting as the blood lumen, of the catheter 20 through which it flows until it emerges through port holes 25*b*, for blood egress, and back into the unobstructed blood vessel 10 downstream of the blockage. The medication or other diagnostic or therapeutic agent 16 flows through the inner lumen (or passage) 31, acting as the agent lumen, of the catheter 20 and, because the end of this passage is sealed at the blockage location, it emerges through port holes 35*m*, for agent egress, near the thrombus or lesion 12. The presence of the blockage forces the medication or other diagnostic or therapeutic agent 16 to re-circulate in the vicinity of the thrombus or lesion 12, thus permeating it completely. The rate of irrigation is controlled by the pressure imposed on the medicated flow and is essentially independent of the blood flow rate. For example, the performance of the catheter as determined by the flow and species transport through it, shall depend on, among other things, its geometrical and dynamical characteristics. The flow of medication or other diagnostic or therapeutic agent 16 merges with the flow of blood 14 where the blood enters through the portholes 24 into the outer lumen 26, acting as the blood lumen, and is discharged with the blood downstream of the blockage.

Figure 3:
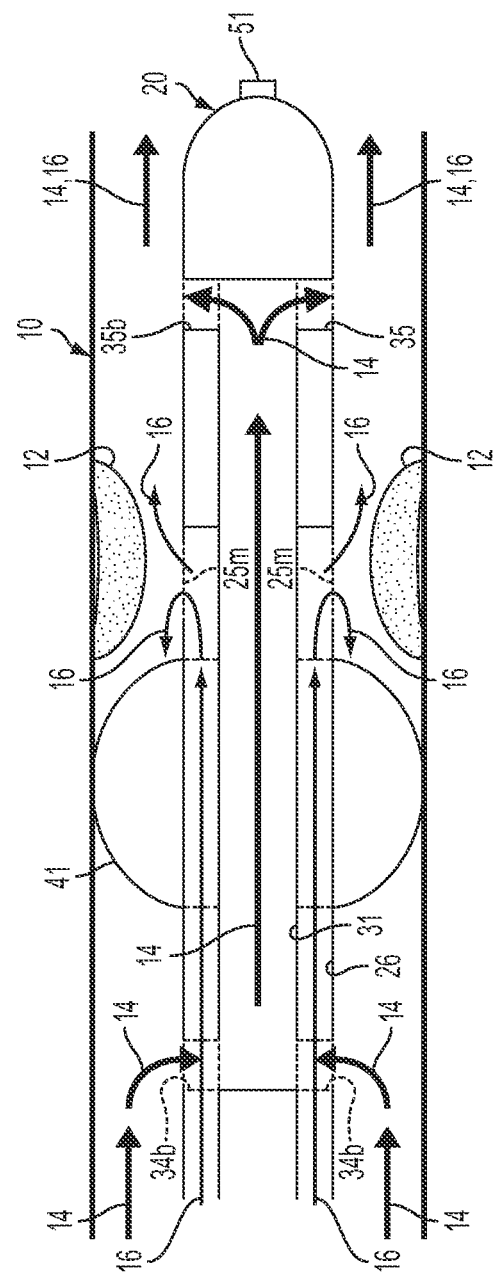
FIGS. 3 and 4 are cross-sectional side views of the catheter design of the present invention located within the lumen of a blood vessel where blood flow is occluded proximal (or partially proximal) to the lesion, and showing blood flow and delivery of an agent through the catheter.

FIG. 3 shows a third possible embodiment of a blood flow by-pass catheter 20 for irrigating thrombi or lesions in a blood vessel 10 with medication or other diagnostic or therapeutic agent 16, or other applicable medium or fluid as desired or required. The flow of blood 14 is blocked by a temporarily enlarged portion or expandable component 41 that may be in direct or indirect communication of the outer lumen 26 (or passage) of the catheter 20 upstream (or at least partially upstream) of the thrombus or lesion 12. This forces the blood 14 to enter through port holes 34*b*, for blood entrance, leading to the hirer lumen 31 (or passage), acting as the blood lumen, of the catheter 20 through which it flows until it emerges through port holes 35*b*, for blood egress, and back into the unobstructed blood vessel 10 downstream of the blockage. The medium, such as medication or other diagnostic or therapeutic agent 16, or as desired or required, flows through an annular passage, acting as the agent lumen, in the outer lumen 26 of the catheter 20 and, because the end of this passage is sealed at the blockage location, it emerges through port holes 25*m*, for agent egress, near the thrombus or lesion 12. The presence of the blockage forces the medication or other diagnostic or therapeutic agent 16 to re-circulate in the vicinity of the thrombus or lesion 12, thus permeating it completely. The rate of Irrigation is controlled by the pressure imposed on the medicated flow and is essentially independent of the blood flow rate. For example, the performance of the catheter as determined by the flow and species transport through it, shall depend on, among other things, its geometrical and dynamical characteristics. The flow of medication or other diagnostic or therapeutic agent 16 exits from the port holes 35*b* and merges with the flow of blood 14 downstream of the blockage and thrombus or lesion 12.

Figure 4:
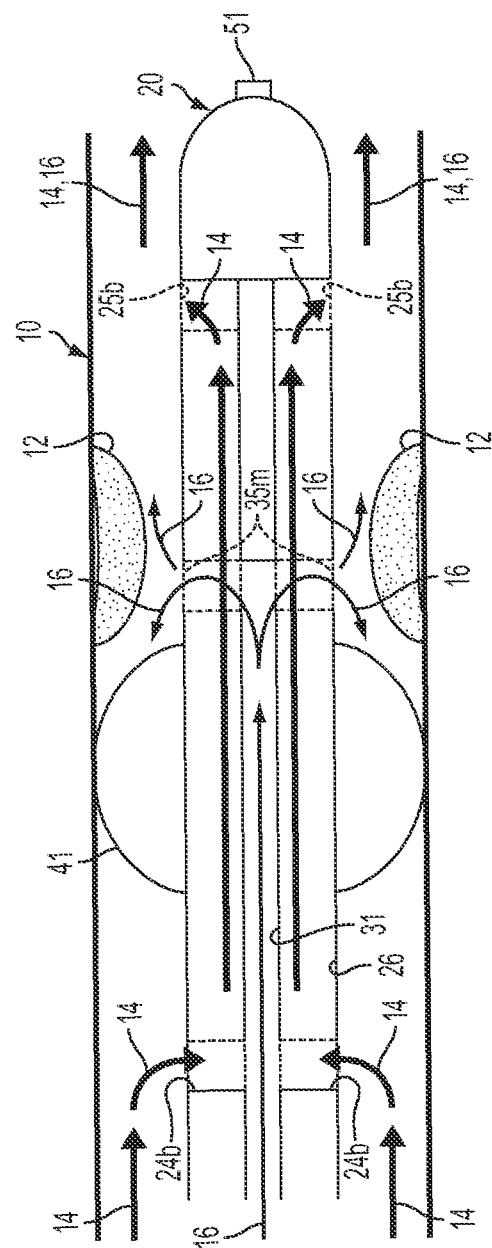

FIG. 4 shows a fourth possible embodiment of a blood flow by-pass catheter 20 for irrigating thrombi or lesion in a blood vessel 10 with a medium, such as medication or other diagnostic or therapeutic agent 16, or other applicable medium or fluid as desired or required. The flow of blood 14 is blocked by a temporarily enlarged portion or expandable component 41 of the outer lumen of the catheter 20 upstream (or at least partially upstream) of the thrombus or lesion 12. This forces the blood 14 to enter through port holes 24*b*, for blood entrance, leading to the outer lumen (passage or annulus) 26, acting as the blood lumen of the catheter 20 through which it flows until it emerges from port holes 25*b*, for blood egress, and back into the unobstructed blood vessel 10 downstream of the blockage and thrombus or lesion 12. The medication or other diagnostic or therapeutic agent 16 flows through the inner lumen 31 (or passage), acting as the agent lumen, of the catheter 20 and, because the end of this passage is sealed just downstream of the blockage location, it emerges through port holes 35*m*, for agent egress, near the thrombus or lesion 12. The presence of the blockage forces the medication or other diagnostic or therapeutic agent 16 to re-circulate in the vicinity of the thrombus or lesion 12, thus permeating it completely. The rate of irrigation is controlled by the pressure imposed on the medicated flow and is essentially independent of the blood flow rate. For example, the performance of the catheter as determined by the flow and species transport through it, shall depend on, among other things, its geometrical and dynamical characteristics. The flow of medication or other diagnostic or therapeutic agent 16 merges with the flow of blood 14 downstream of the blockage and thrombus or lesion 12.

Figure 5:
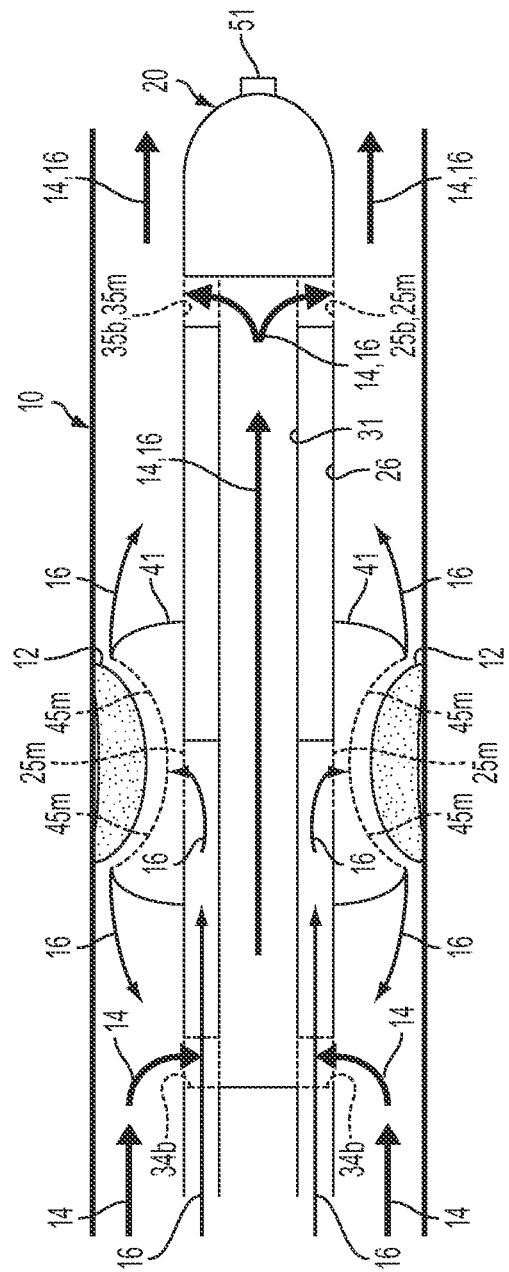
FIG. 5 is a cross-sectional side view of the catheter design of the present invention located within the lumen of a blood vessel where blood flow is occluded around the lesion (or partially around the lesion), and showing blood flow and delivery of an agent through the catheter.

FIG. 5 schematically illustrates a fifth possible embodiment of a blood flow by-pass catheter 20 for irrigating thrombi or lesions in a blood vessel 10 with a medium, such as medication or other diagnostic or therapeutic agent 16, or other applicable medium or fluid as desired or required. The flow of hood 14 is blocked by a temporarily enlarged portion or expandable component 41 of the outer lumen 26 (or passage) of the catheter 20 surrounding (or at least partially surrounding) the thrombus or lesion 12. This forces the blood 14 to enter through port holes 34b, for blood entrance, leading to the inner lumen 31, acting as the blood lumen, of the catheter 20 through which it flows until it emerges from port holes 35b, for blood egress, and back into the unobstructed blood vessel 10 downstream of the blockage. The medication or other diagnostic or therapeutic agent 16 flows through an annular passage, acting as the agent lumen, in the outer lumen 26 (or passage) of the catheter 20 and, because the end of this passage is sealed at the blockage location, it emerges through port holes 25m, of the outer lumen 26 for agent egress, in, through or transverse to the temporarily enlarged lining or expandable component 22 of the outer lumen 26 that surrounds or at least partially surrounds the thrombus or lesion 12. The medication or other diagnostic or therapeutic agent 16 seeps through openings 45m in this porous lining (or other functional port holes) to bathe the thrombus or lesion 12 and permeates it completely. The rate of irrigation is controlled by the pressure imposed on the medicated flow and is essentially independent of the blood flow rate. For example, the performance of the catheter as determined, by the flow and species transport through it, shall depend on, among other things, its geometrical and dynamical characteristics. The flow of medication or other diagnostic or therapeutic agent 16 merges with the flow of blood 14 on either side of the thrombus or lesion 12 and is eventually carried downstream in the blood vessel 10.

FIG. 6 schematically illustrates a sectional view VI-VI of an embodiment of the blood flow by-pass catheter 20 provided in FIG. 1. The catheter 20 contains an outer lumen (passage or annulus) 26 and an inner lumen (passage) 31. Either lumen can be used for the flow of blood or medium (e.g., medication), or inflating the means for blocking the flow of blood and/or medium.

Figure 7:
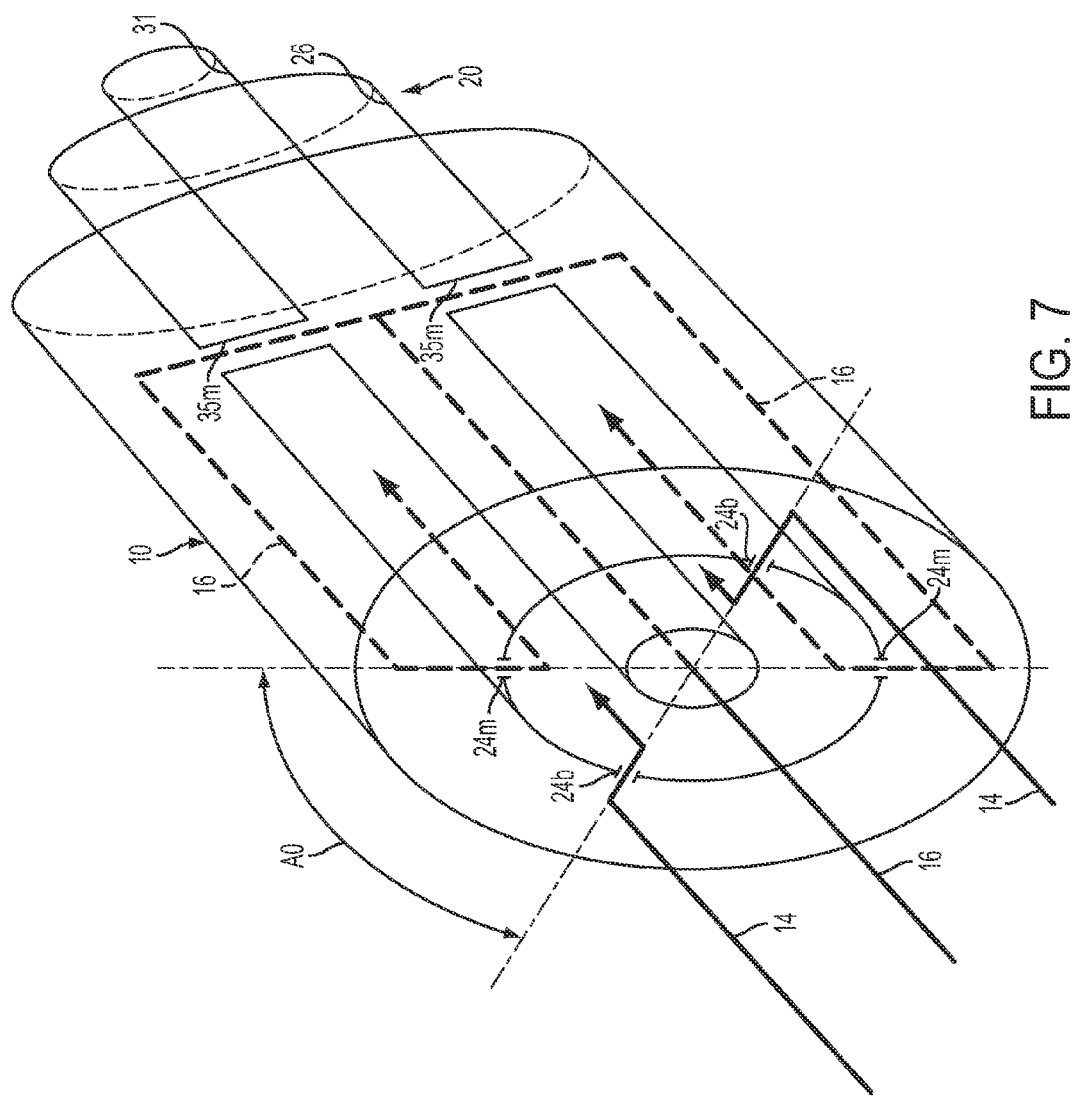
FIG. 7 schematically illustrates a perspective partial view taken at cross-sectional view VII-VII of the blood flow by-pass catheter provided in FIG. 2.

FIG. 7 schematically illustrates a perspective partial view taken at cross-section VII-VII of the blood flow by-pass catheter 20 provided in FIG. 2. The catheter 20 contains an outer lumen (passage or annulus) 26 and an inner lumen (passage) 31. Either lumen can be used for the flow of blood or medium (e.g., medication), or inflating the means for blocking the flow of blood and/or medium. Referring, to the partial view of the embodiment shown in FIG. 2, provided is blood flow by-pass catheter 20 for irrigating thrombi or lesions in a blood vessel 10 with a medium, such as a medication or other diagnostic or therapeutic agent 16, or other applicable medium or fluid as desired or required. The flow of blood 14 is blocked by a temporarily enlarged portion or expandable component 41 (not shown) that may be in direct or indirect communication of the outer lumen (or passage) 26 of the catheter 20 downstream (or at least partially downstream) of the thrombus or lesion 12. This forces the blood 14 through port holes 24b, for blood entrance, leading to the outer lumen (passage or annulus) 26, acting as the blood lumen, of the catheter 20 through which it flows until it emerges through port holes 25b, for blood egress, and back into the unobstructed blood vessel 10 downstream of the blockage. The medication or other diagnostic or therapeutic agent 16 flows through the inner lumen (or passage) 31, acting as the agent lumen, of the catheter 20 and, because the end of this passage is sealed at the blockage location (not shown), it emerges through port holes 35m, for agent egress, near the thrombus or lesion 12. The presence of the blockage forces the medication or other diagnostic or therapeutic agent 16 to re-circulate in the vicinity of the thrombus or lesion 12, thus permeating it completely. It should be appreciated that angular off set (as designated by the angle referenced as AO) of the inlet passage, via port holes 24b for blood entrance, and inlet let passage, via port holes 24m for medium entrance, is along the circumference of the outer lumen or passage 26. It should further be appreciated that these portholes may be arranged in a variety of ways or locations along the circumferential and axial (e.g., longitudinal) directions of the lumens.

For the purpose of simplifying the drawings, FIGS. 1-7 may have been illustrated having various port holes 24b, 24m, 34b, 34m aligned circumferentially or axially (e.g., longitudinally) with one another. However, it should be appreciated that the various port holes 24b, 24m, 34b, 34m may be arranged in a variety of locations and ways circumferentially and axially (e.g., longitudinally) along the inner lumen 31 (inner passage) and outer lumen 26 (outer passage) in support of the present invention discussed throughout. The dimensions, shapes, contours and angular alignment of the port holes (including conduit/channel of the portholes) may be varied and designed according to the principals and aspects of the present invention.

These particular geometrical configurations of the bypass catheter (as discussed in FIGS. 1-7 and through this document) allow for active hydrodynamic control of the medication stream flow (i.e., applicable medium stream) and of the concentration of medication in it, as well as the distribution of medication (i.e., applicable medium) in the vicinity of the thrombus, to achieve a specific result. Note that the openings or portholes allowing the flow of blood to bypass the thrombus (or lesion) by entering the inner lumen or passage, and the openings allowing the medication stream to exit the outer lumen or passage, are periodically or selectively distributed around (i.e., circumferentially) the catheter in each case. Alternatively, it should be noted that the openings or portholes allowing the now of blood to bypass the thrombus (or lesion) by entering the outer lumen, and the openings allowing the medication stream to exit the inner lumen, are periodically or selectively distributed around (i.e., circumferentially) the catheter in each case.

As one departure point from various of the existing empirical and/or trial-and-error designs described in the prior art for such devices, with regards to aspects of various embodiments of the present invention catheter devices, systems and related methods we emphasize in what follows that these inlet and exit openings can be selectively shaped, staggered and positioned in the circumferential and/or axial (e.g., longitudinal) directions in order to generate non-intuitive patterns of placement that will result in highly three-dimensional, well-mixed flow patterns in the vicinity of the thrombus or lesion, thus benefiting its irrigation and maximizing the medication dwell time, such as concentration and dwell time optimization.

Figure 8:
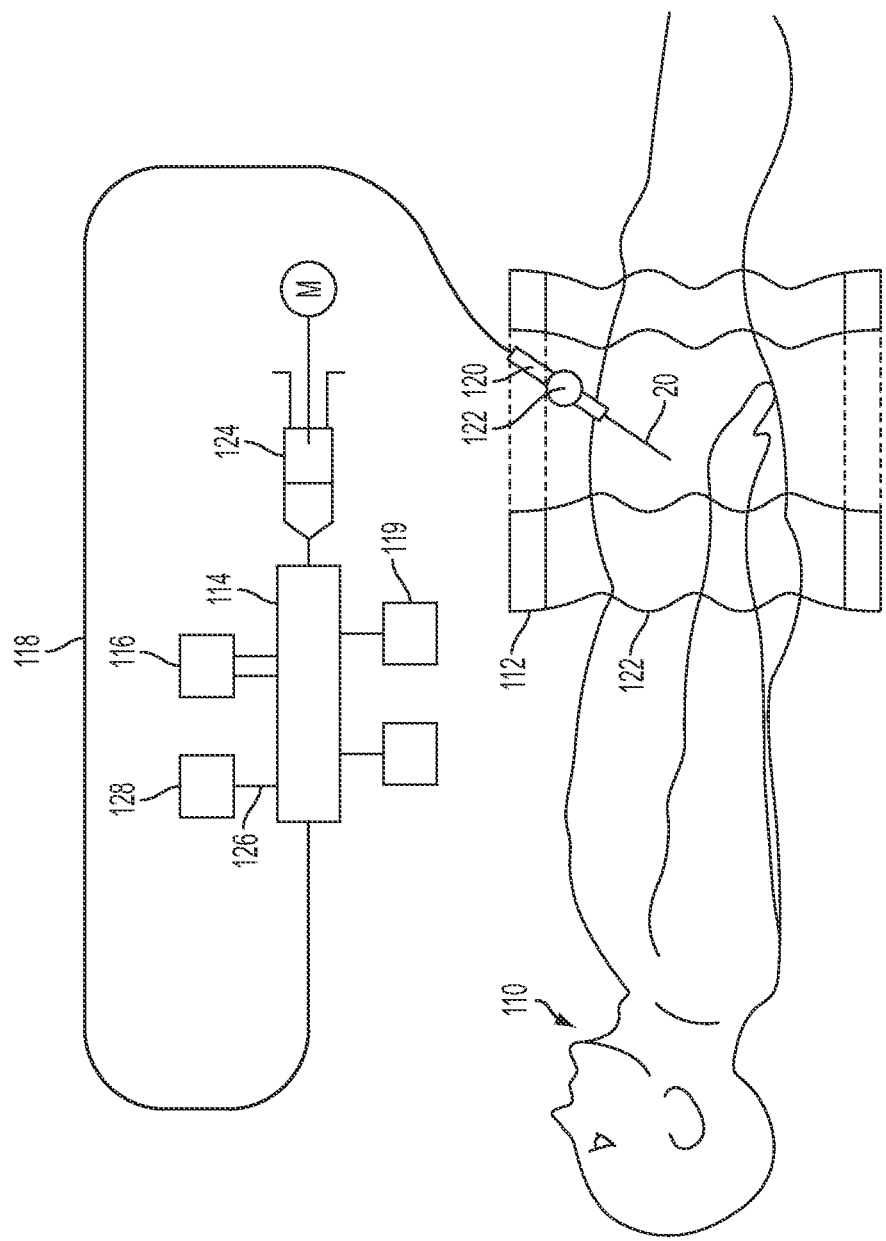
FIG. 8 is a schematic diagram showing a subject undergoing an examination and/or intervention inside or in communication with the bore, component or module of an imaging system (or guidance, navigation or tracking system) whereby a catheter device is disposed within the subject.

Turning to FIG. 8, FIG. 8 is a schematic diagram showing a patient 110, or any subject or object, undergoing an examination and/or intervention inside or in communication with the bore, component or module of an imaging system 112 whereby a catheter device 20 is disposed within the patient. It should be appreciated that the imaging system 112 may be operative relative to any part, parts, vasculature, duct, cavity or anatomy of the patient, subject or object as desired or required for the applicable practice, method, treatment, therapy or procedure. Various embodiments of the catheter device 20, method of using the catheter device, and method of manufacturing the catheter device are capable of being adapted for various purposes and are not limited to use with the following imaging systems 112 including, but not limited thereto, the following: magnetic resonance imaging (MRI) systems, CT systems, radiotherapy systems, fluoroscopy systems, X-ray imaging systems, ultrasound systems, vascular imaging systems, nuclear imaging systems, positron emission tomography, magnetic resonance angiography, and magnetic resonance spectroscopy systems, and the like. A manifold 114 couples several therapeutic or diagnostic devices typified by device 116 (or device for any applicable agent, substance, or material) to the delivery catheter 118. A syringe, flow-driver or pumping device 124 is also in communication with the manifold 114. The cell delivery catheter 118 in turn may be delivered through a guide sheath 120 that may be positioned in a navigation guide 122. In operation the physician or user inserts the catheter device 118 into the blood vessel (or other anatomy part or duct or subject region) under image system guidance (e.g., MRI guidance or other applicable examination or intervention or imaging system discussed herein). The same or similar imaging visualization or MRI visualization may be used to follow the progress of the implant both acutely and chronically. This specific version of the catheter 20 within the concepts disclosed herein may have any of the attributes or related methods of use and manufacture as described herein. The catheter device 20, as well as the delivery catheter 118, may have various interior and peripheral ports, lumens and related elements within the context of the disclosure provided. Such interior and peripheral ports, lumens and related elements may be used to deliver other devices and perform various diagnostic functions. For example, each lumen, port and related catheter element may communicate with a separate port of the manifold 114. A lumen, chamber or channel may contain a sensor or transducer 128, such as a pressure transducer, species concentration senor, fluid motion stress sensor, or heat sensor, as well as other desired or required transducers or sensors. Other lumens and channels may be devoted to an optical cell counter device, for example. Such a device may operate with a plurality of fibers located in one or more separate lumens and/or ports to measure the number of and viability of cells or medium delivered by the catheter. An example of fiber optics related application/technology is discussed in U.S. patent application Ser. No. 10/444,884, fried May 23, 2003 (U.S. 2003/0204171, published Oct. 30, 2003), of which is hereby incorporated by reference herein in its entirety.

The blood and medication streams flowing through the catheter designs of interest, such as those shown in FIGS. 1-8, may be unsteady, three-dimensional ad laminar, and to correspond to incompressible constant property fluids. The fluid stream passing through the core of the catheter is pulsating blood and that passing through the lumen and containing the medication is essentially water (saline). Initially, we assume the blood to be a Newtonian fluid since this significantly simplifies the analysis of the problem. The assumption is valid provided the shear rates involved are above $1000\ s^{-1}$ (see: Cokelet G R: The Rheology and Tube Flow of Blood (Chapter 14) in Skalak R, Chien S (eds.): *Handbook of Bioengineering,* McGraw-Hill, New York, 1987, of which is hereby incorporated by reference herein in its entirety). For this condition whole blood with normal hematocrit (about 45%) can generally be considered a Newtonian fluid with a viscosity of about 4.2 cP at 37° C., about 1.8 times the viscosity of water at the same temperature (see: Schneck D: Cardiovascular Mechanics, in Enderle J, Blanchard S and Bronzino J, eds., Chapter 10, *Introduction to Biomedical Engineering*. Academic Press, New York, 2000, of which is hereby incorporated by reference herein in its entirety). At shear rates below about $100\ s^{-1}$, blood becomes non-Newtonian and viscosity increases as shear rate decreases. The main reasons are reversible cell-cell aggregation and cell deformability. If necessary during the computational design process, the Newtonian assumption for blood can be relieved in favor of a more appropriate constitutive relation connecting the viscous stress to the rate of strain.

To achieve the best-case configurations of the devices shown in FIGS. 1-8, for example, computational fluid dynamics is employed within the framework of an adaptive problem-solving methodology based on the use of Global Optimization methods, such as Genetic Algorithms (GAs), thus allowing optimal catheter design(s). Aspects of various embodiments of the present invention provide, but not limited thereto, a strategy to dynamically accumulate information and use it to improve problem-solving performance this end, we combine the numerical solution of flow and mass transport conservation equations, for different catheter geometries and flow conditions, with an adaptive solution methodology based on the use of Global Optimization methods, such as GAs, to determine optimal catheter performance. As well as other types of available optimization algorithm methods that are available and suitable and appropriate for such applications.

Genetic Algorithms (GA) belong to the class of Global Optimization methods that include, for example but not limited thereto, simulated annealing, multistart and interval methods, continuous branch and bound methods, evolutionary algorithms, and tabu search and scatter search methods, as well as other Global Optimization methods not specifically enumerated herein. A goal of a Global Optimization method is to determine the absolutely best answer for problems, systems or procedures that offer a number of possible solutions. A feature of the GA methodology is its robustness. Whereas Calculus-based optimization and search (hill-climbing) methods lack robustness. Calculus-based optimization and search (hill-climbing) methods are local in scope and, once a minimum or maximum is found, require random restarts to initiate searches for other minima/maxima. Also, calculus-based methods require the existence of derivatives whereas many practical problems present parameter spaces that do not possess well defined slope values. Further, a drawback with regard to enumerative methods is that enumerative methods systematically search for all solutions of an optimization problem in the parameter space, one at a time. However, because any meaningful problem presents an extremely large number of possible solutions in the parameter space it is impracticable to enumerate them all by utilizing the enumerative methods. This lack of efficiency accounts for the lack of robustness of enumerative methods. Still further, random search algorithms have been developed to overcome the deficiencies of calculus-based and enumerative methods but, in the end, random search algorithms also suffer from the lack of efficiency associated with enumerative methods. In contrast, the robustness of the GA method, for example, lies in the use of random choice as a tool to guide an extremely exploitative search based on an appropriate coding of the relevant parameter space.

The present solution methodology will work in a way similar to a classical control theory standard feedback loop, wherein a complex process (here the performance of a catheter as determined by the flow and species transport through it, which depend on its geometrical and dynamical characteristics) is connected to an adaptive solution strategy (the GA) via a feedback loop. Subject to input data such as catheter dimensions and flow and medication species boundary conditions, the conservation equations yield field solutions for the primary variables of interest like velocity, pressure and species concentration, and for secondary quantities derived from the primary like shear stresses and mass fluxes. The primary and secondary quantities allow the evaluation of a preformulated performance measure and part of this numerical output is the input to the adaptive strategy used to optimize the catheter design. The adaptive strategy is responsible for the dynamical accumulation of decision-making information through the feedback portion of the loop. It also generates the control actions that modify a current set of dimensions, variables, or parameters with the expectation that the changes will improve the catheter's performance. The description of the adaptive solution strategy using GAs provided here follows closely that given by Queipo N, Devarakonda R and Humphrey J A C: Genetic Algorithms for Thermosciences Research: Application to the Optimized Cooling of Electronic Components, Int. J. Heat and Mass Transfer 37:893-908, 1994, of which is hereby incorporated by reference herein in its entirety.

A GA is an adaptive search procedure loosely based on the Darwinian notion of evolution by natural selection (see, for instance, Davis L (Editor): *Handbook of Genetic Algorithms*. Van Nostrand Reinhold, New York, 1991, of which is hereby incorporated by reference herein in its entirety). It uses rules of natural selection to investigate highly complex, multidimensional, multivariable problems. GAs have been employed in a variety of search, optimization and machine learning applications in science and engineering where other more traditional methods either fail or are subject to significant limitations. Such an approach has been applied successfully by Humphrey and coworkers (Queipo N, Devarakonda R and Humphrey J A C: Genetic Algorithms for Thermosciences Research: Application to the Optimized Cooling of Electronic Components. Int. J. Heat and Mass Transfer 37:893-908, 1994, of which is hereby incorporated by reference herein in its entirety; Queipo N, Humphrey J A C and Ortega A: Multiobjective Optimal Placement of Convectively Cooled Electronic Components on Printed Wiring Boards. IEEE Transactions on Components, Packaging, and Manufacturing Technology, Part A 21:142-153, 1988, of which is hereby incorporated by reference herein in its entirely) to find optimal arrangements of electronic components, as well as optimal conditions of the flows going past them, such that their convective cooling is maximized and none is destroyed by overheating.

The objects to be optimized geometrically and dynamically here are the double lumen bypass catheters depicted in, for example, FIGS. 1-8. For this, it is necessary to find the optimal or nearly optimal values of a set of variables and/or their related parameters that minimize a cost function, and/or maximize a corresponding per measure, while satisfying all imposed problem constraints. For example, the variables could be, but not limited thereto, the following: a) the geometrical shapes and dimensions of the catheter passages; b) the relative locations and orientations of the various inlet and exit flow planes; c) the velocity components, pressure, and concentration at specific locations of blood and/or medium inside and outside the catheter; d) the shear stresses of the flows inside and outside the catheter; and/or e) the concentration and residence time of medication species in the vicinity of the thrombus. Related parameters could be, but not limited thereto, the Reynolds, Schmidt and/or Pulsating Flow parameters. Constraints could be, but not limited thereto, the following: a) the maximum or minimum allowed sizes of the catheter and of its passage dimensions; b) the maximum allowed flow speeds and/or shear stresses; c) the maximum allowed pressure drop and skin friction; e) the maximum allowed medication concentration; and/or f) the overall expected elapsed time needed for treatment. The performance measure to be maximized is usually a complicated multidimensional function of quantities like the above and, often, it is multimodal, possessing several local maxima or minima.

It should be appreciated that an aspect of the various embodiments of the present invention is to provide, among other things, a geometrically and dynamically optimized physical catheter for fabrication and practical use based on a numerical optimization process. Further, an aspect of the various embodiments of the present invention is to provide, among other things, the capability to design and test a catheter, and which may be assisted by experimentation. Various embodiments of the present invention catheter may use solutions of the conservation equations for different geometrical and dynamical renditions of the catheter as the data base from which to determine one or more optimal catheter designs. For this, the GA requires initial input values associated with an initial set of possible flow and concentration field solutions to commence the search for an optimal solution corresponding to one (or more) optimal catheter designs. Through a process based on concepts taken from evolution and using rules of natural selection, the GA improves upon these solutions. In any calculation cycle, the set of candidate solutions at time t, P(t), operated upon by the GA is called the population and each member of this set or generation, when encoded as a string of symbols, is called a chromosome. Originally pioneered by Holland (Holland J H: *Adaptation in Natural and Artificial Systems*, MIT Press, Cambridge, Mass., 1975, of which is hereby incorporated by reference herein in its entirety), a GA may be abstractly represented by the following sequence of operations:

t=0;
Initialize.P(t);
Evaluate P(t);
While (termination condition not satisfied) do
begin
t=t+1;
Select P(t);
Recombine Pt(t);
Evaluate P(t);
end.

In this representation each iteration in the 'while' loop produces a new generation of candidate solutions, also encoded as chromosomes. Thus, if a set of candidate solutions is properly encoded, and the 'Select' procedure and the GA operators of the 'Recombine' procedure are appropriately chosen, each generation of parent solutions will produce a generation of children solutions (the new set of candidate solutions) which, in general, will have an average performance better than the parent generation. It is the role of the GA operators to construct and propagate the features of the schema of those chromosomes responsible for the improved performance of some candidate solutions relative to others. The schema reveals the subset or chromosomes possessing similarities at certain chromosome positions and the schemata derived from good chromosome solutions within a generation provide the building blocks from which to synthesize improved solutions in the offspring generation.

For illustration purposes, let us consider a highly simplified example. With reference to the catheter geometry shown in the top schematic of FIG. 1, call $\Delta P_M$ the time-averaged pressure drop between the inlet and exit locations of the medication stream and call $[\omega_M]_T$ the time-averaged concentration of the medication species in the vicinity of the thrombus. Let us define a cost function or performance measure CF that rewards increases in $[\omega_M]_T$ and penalizes increases in $\Delta P_M$. The simplest function is $CF=\alpha[\omega_M]_T - \beta \Delta P_M$, where $\alpha$ and $\beta$ are weights given to $[\omega_M]_T$ and $\Delta P_M$, respectively. Suppose, also, it is found that $[\omega_M]_T^\infty \Delta P_M$ so that it is not possible to decrease $\Delta P_M$ (favorable) without decreasing $[\omega_M]_T$ (unfavorable). The question then is What catheter geometry will minimize $\Delta P_M$ while maximizing $[\omega_M]_T$ in order to maximize CP?

Let us further assume, also for illustration purposes, we find that the three most critical geometrical parameters bearing on the maximization of CF are the linter diameter $D_b$ of the passage through which the blood flows, the annulus gap size $D_m$ of the passage through which the medication steam (or applicable medium) flows, and the distance $L_{i-e}$ between the inlet and exit planes for the medication stream. For example, the distance $L_{i-e}$ would be due to the angular off set that the inlet passage and out let passage is along the circumference of the lumen(s). If we encode these quantities in microns using a 13 unit binary numbering scheme, then any of them can, in principle, range between 0000000000000 and 1111111111111 or, equivalently, between 0 and 8191 µm. Suppose we find via numerical calculation of the flow and medication species fields that the largest value of CF corresponds to $D_b$500 µm, $D_m$=250 µm and $L_{i-e}$=8000 µm. Then the $D_b$-$D_m$-$L_{i-e}$ chromosome corresponding to this geometry is given by 0010111110000-0101111100000-0000001011111. Generally, it is expected that the flow and mass transport characteristics of the optimal catheter geometry represented by this chromosome will differ from other less optimal (or unacceptable) geometries given by chromosomes such as, for example, 001011 0110000-0101111100000-0000101011111 and 000011 1110001-0101100100000-0000001111101. Note, however, that by exchanging the highlighted units in the first and third genes of these two chromosomes the original optimal chromosome results.

Thus, it is an objective of the adaptive search strategy, based on the use of the GA to find the chromosome(s) corresponding to the optimal catheter(s) from among a very large number of alternative possibilities evolving under imposed natural selection rules. For example, assuming integer increments of ±1 µm, the number of distinct chromosomes based on the three-gene $D_b$-$D_a$-$L_{i-e}$ sequence above is already N=500×250×8000–$10^9$. Further, it should be appreciated that the inclusion of additional genes (representing other important geometrical or dynamical features) in the chromosome makes the number of potentially possible solutions even larger. Notwithstanding, the power of the GA approach resides in its ability to home in on optimal or near optimal chromosomes (representing optimal catheter designs) within a few generations.

In a typical GA, the initial set of candidate solutions or encoded chromosomes (in the present case, the geometrical and dynamical characteristics of a catheter) is usually selected randomly. However, preliminary calculations (or experimental results) can help narrow down the range of values. There appear to be no definitive rules regarding the best initial solution population size for a given problem but guidelines are given in Grefenstette J J: Optimization of Control Parameters for Genetic Algorithms. IEEE Trans. Systems, Man Cybernetics SMC-16 (1):122-128, 1986, of which is hereby incorporated by reference herein in its entirety. The candidate solutions are encoded as fixed-length chromosomes for which different encoding schemes, such as binary as illustrated above) and integer, have been used.

In the GA operation sequence defined above, the 'Evaluate' procedure calculates the fitness of each chromosome; this is the measure of performance associated with each candidate solution. It is an important quantity since the probability that a chromosome in the parent population will contribute its schema to the offspring generation is proportional to the chromosome's relative fitness. The function of the 'Select' procedure is to specify the actual number of offspring that each parent chromosome contributes to the next generation based on the relative performance of that chromosome. Different selection mechanisms are discussed in Baker J E: Reducing bias and efficiency in the selection algorithm. *Proceedings of the Second International Conference on Genetic Algorithms*, pp. 14-21. Lawrence Erlbaum, Hillsdale, N.J., 1987, of which is hereby incorporated by reference herein in its entirety. The 'Recombine' procedure contains the GA operators that are expected to construct and propagate the schema responsible for good performance. The most prominent GA 'Recombine' operators are crossover and mutation. The crossover operator acts on two chromosomes at a time, on average generating fitter offspring by combining the schema in each parent. The mutation operator usually involves the infrequent random alteration of the value of one or more bits in a chromosome. Crossover and mutation operators for binary chromosomes and, because they can also disrupt desirable schema, it is important to specify them appropriately in the GA. In a GA application, the Select, Recombine and Evaluate procedures are repeated from generation to generation until some pre-established convergence or termination criterion is satisfied.

Figure 9:
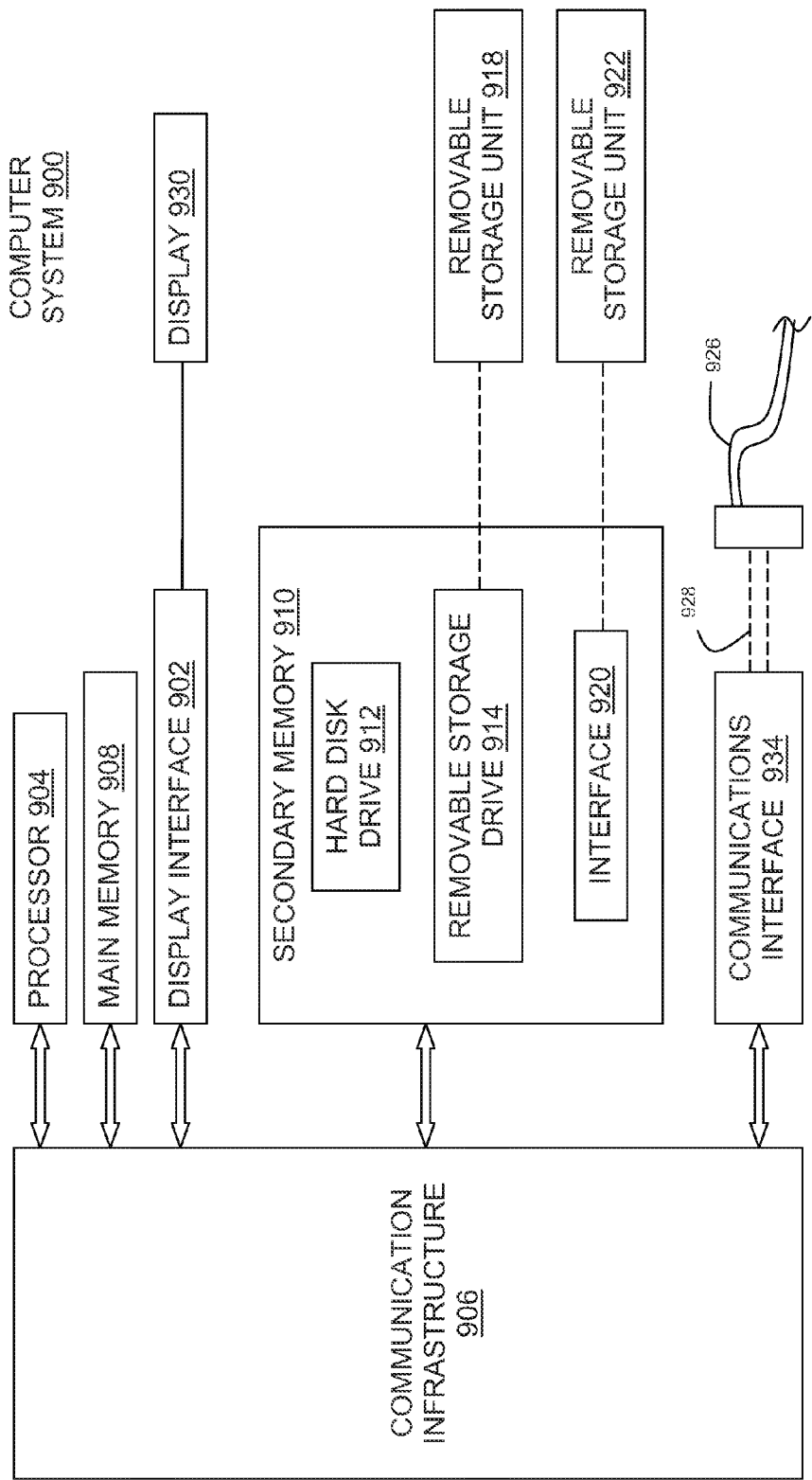
FIG. 9 is a functional block diagram for a computer system for implementation of an exemplary embodiment or portion can embodiment of present invention.

Turning to FIG. 9, FIG. 9 is a functional block diagram for a computer system 900 for implementation of an exemplary embodiment or portion of an embodiment of present invention. For example, a method of an embodiment of the present invention may be implemented using hardware, software or a combination thereof and may be implemented in one or more computer systems or other processing systems, such as personal digit assistants (PDAs), operated to achieve the best-case or optimized configurations of the catheter devices shown in FIGS. 1-8 and discussed throughout. For example, the processing of computational fluid dynamics may be employed within the framework of an adaptive problem-solving methodology that is based on the use of present invention Global Optimization methods and techniques, such as Genetic Algorithms (GAs) that allow for optimal or best-case catheter device design(s).

In an example embodiment, an embodiment of the invention was implemented in software running on a general purpose computer 900 as illustrated in FIG. 9. Computer system 900 includes one or more processors, such as processor 904 Processor 904 is connected to a communication infrastructure 906 (e.g., a communications bus, cross-over bar, or network). Computer system 900 may include a display interface 902 that forwards graphics, text, and other data from the communication infrastructure 906 (or from a frame buffer not shown) for display on the display unit 930.

Computer system 900 also includes a main memory 908, preferably random access memory (RAM), and may also include a secondary memory 910. The secondary memory 910 may include, for example, a hard disk drive 912 and/or a removable storage drive 914, representing a floppy disk drive, a magnetic tape drive, an optical disk drive, a flash memory, etc. The removable storage drive 914 reads from and/or writes to a removable storage unit 918 in a well known manner. Removable storage unit 918, represents a floppy disk, magnetic tape, optical disk, etc. which is read by and written to by removable storage drive 914. As will be appreciated, the removable storage unit 918 includes a computer usable storage medium having stored therein computer software and/or data.

In alternative embodiments, secondary memory 910 may include other means for allowing computer programs or other instructions to be loaded into computer system 900. Such means may include, for example, a removable storage unit 922 and an interface 920. Examples of such removable storage units/interfaces include a program cartridge and cartridge interface (such as that found in video game devices), a removable memory chip (such as a ROM, PROM, EPROM or EEPROM) and associated socket, and other removable storage units 922 and interfaces 920 which allow software and data to be transferred from the removable storage unit 922 to computer system 900.

Computer system 900 may also include a communications interface 924. Communications interface 924 allows software and data to be transferred between computer system 900 and external devices. Examples of communications interface 924 may include a modem, a network interface (such as an Ethernet card), a communications port (e.g., serial or parallel, etc.), a PCMCIA slot and card, a modem, etc. Software and data transferred via communications interface 924 are in the form of signals 928 which may be electronic, electromagnetic, optical or other signals capable of being received by communications interlace 924. Signals 928 are provided to communications interface 924 via a communications path (i.e., channel) 926. Channel 926 carries signals 928 and may be implemented using wire or cable, fiber optics, a phone line, a cellular phone link, an RE link, an infrared link, wireless link or connection and other communications channels.

In this document, the terms "computer program medium" and "computer usable medium" are used to generally refer to media such as removable storage drive 914, a bard disk installed in hard disk drive 912, and signals 928. These computer program products are means for providing software to computer system 900. The invention includes such computer program products.

Computer programs (also called computer control logic) are stored in main memory 908 and/or secondary memory 910. Computer programs may also be received via communications interface 924. Such computer programs, when executed, enable computer system 900 to perform the features of the present invention as discussed herein. In particular, the computer programs, when executed, enable processor 904 to perform the functions of the present invention. Accordingly, such computer programs represent controllers of computer system 900.

In an embodiment where the invention is implemented using software, the software may be stored in a computer program product and loaded into computer system 900 using removable storage drive 914, hard drive 912 or communications interface 924. The control logic (software), when executed by the processor 904, causes the processor 904 to perform the functions of the invention as described herein.

In mother embodiment, the invention is implemented primarily in hardware using, for example, hardware components such as application specific integrated circuits (ASICs). Implementation of the hardware state machine to perform the functions described herein will be apparent to persons skilled in the relevant arks).

In yet another embodiment, the invention is implemented using a combination of both hardware and software.

In an example software embodiment of the invention, the methods described above were implemented in SPSS control language, but could be implemented in other programs such as, but not limited to, C++ programming language or other programs available to those skilled in the art.

The devices, methods and computer program product of various embodiments of the present invention discussed throughout may be practiced and implemented with the methods, systems and devices disclosed in the following U.S. patents and U.S. Patent Application Publications, and of which are hereby incorporated by reference herein in their entirety:

U.S. Pat. No. 6,840,949 to Barbut, entitled "Devices and Methods for Preventing Distal Embolization Using Flow Reversal in Arteries Having Collateral Blood Flow;"

U.S. Pat. No. 6,830,579 to Barbut, entitled "Devices and Methods for Preventing Distal Embolization Using Flow Reversal and Perfusion Augmentation Within the Cerebral Vasculature;"

U.S. Pat. No 6,830,577 to Nash et al., entitled "System and Method of Use for Treating Occluded Vessels and Diseased Tissue;"

U.S. Pat. No. 6,796,992, to Barbut, entitled "Cerebral Perfusion Augmentation;"

U.S. Pat. No. 6,790,204 to Zadno-Azizi et al., entitled Method for Containing and Removing Occlusions in the Carotid Arteries;"

U.S. Pat. No. 6,767,345, to St. Germain et al., entitled "Partial Aortic Occlusion Devices and Methods for Renal and Coronary Perfusion Augmentation;"

U.S. Pat. No. 6,755,846, to Yadav, entitled "Vascular Filter;"

U.S. Pat. No. 6,743,208 to Coyle, entitled "Occlusion Balloon Catheter with Distal Valve;"

U.S. Pat. No. 6,743,196 to Barbut et al., entitled "Partial Aortic Occlusion Devices and Methods for Cerebral Perfusion Augmentation;"

U.S. Pat. No. 6,733,474 to Kusleika, entitled "Catheter for Tissue Dilatation and Drug Delivery;"

U.S. Pat. No. 6,730,063 to Delaney et al., entitled "Catheter Devices and Methods for Their Use in the Treatment of Calcified Vascular Occlusions;"

U.S. Pat. No. 6,712,806 to St. Germain et at, entitled "Partial Aortic Occlusion Devices and Methods for Cerebral Perfusion Augmentation;"

U.S. Pat. No. 6,712,798 to Constantz, entitled "Multilumen Catheters and Methods for Their Use;"

U.S. Pat. No 6,660,021 to Palmer et at entitled "Intravascular Device and System;"

U.S. Pat. No. 6,635,046 to Barbut, entitled "Partial Aortic Occlusion Devices and Methods for Cerebral Perfusion Augmentation;"

U.S. Pat. No. 6,613,076 to Cherif-Cheikh, entitled "Implantable Intraluminal Device;"

U.S. Pat. No. 6,592,557 to Barbut, entitled "Partial Aortic Occlusion Devices and Methods for Cerebral Perfusion Augmentation;"

U.S. Pat. No. 6,582,448 to Boyle et al., entitled "Vessel Occlusion Device for Embolic Protection System;"

U.S. Pat. No. 6,565,552 to Barbut, entitled "Partial Aortic Occlusion Devices and Methods for Cerebral Perfusion Augmentation;"

U.S. Pat. No. 6,558,401 to Azizi, entitled "Low Profile Catheter for Angioplasty and Occlusion;"

U.S. Pat. No. 6,558,356 to Barbut, entitled "Medical Device for Flow Augmentation in Patients With Occlusive Cerebrovascular Disease and Methods of Use;" U.S. Pat. No. 6,533,800 to Barbut, entitled "Devices and Methods for Preventing Distal Embolization Using Flow Reversal in Arteries Having Collateral Blood Flow;"

U.S. Pat. No. 6,533,767 to Johansson et al., entitled "Methods for Enhancing Fluid Flow Through an Obstructed Vascular Site;"

U.S. Pat. No. 6,506,180 to Lary, entitled "Passive Perfusion Sleeve/Placement Catheter Assembly;"

U.S. Pat. No. 5,792,105 to Lin et al., entitled Multichannel Balloon Catheter for Delivering Fluid;"

U.S. Pat. No. 5,254,089 to Wang, entitled "Medication Dispensing Balloon Catheter;"

U.S. Pat. No. 5,021,044 to Sharkawy, entitled "Catheter for Even Distribution of Therapeutic Fluids;" and U.S. Pat. Application Publication No. 2004/0162519 A1 to Helkowski et al., entitled Aortic Occlusion Balloon Cannula."

One skilled in the art can see that many other embodiments of the lumens and number of lumens, annular passages, means for flow-blockage, flow channeling and recirculation, and other details of construction and use constitute non-inventive variations of the novel and insightful conceptual means, system and technique which underlie the present invention.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in an claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein, in the event of such conflict, including a conflict that would render invalid any claim herein or seeking priority hereto, then any such conflicting information in such incorporated by reference material is specifically not incorporated by reference herein.

We claim:

1. A catheter device for insertion into a vascular structure or body duct, said catheter device having a distal end and a proximal end for delivery of a medium to a lesion, said device comprising:

a blood lumen for allowing blood to pass there through;

a medium lumen for the delivery of a medium to the lesion, said medium lumen comprising at least one medium egress port for communication with the lesion;

an expandable component disposed on said catheter device to block or impede the vascular flow of blood in the vascular structure or body duct; and said blood lumen comprising at least one blood entrance port proximally before said expandable component to allow blood to enter and at least one blood egress port distally beyond said expandable component to allow blood to pass distally beyond said expandable component, wherein, a position of said inlet ports and said exit ports is determined by application of a global optimization algorithm comprising:

selecting variables including:

a) geometrical shapes and dimensions of at least one of said blood lumen and said medium lumen, b) relative locations and orientations of flow planes of at least one of said blood entrance port and blood egress port, and c) concentration and residence time of the medium in the vicinity of a specific location outside said catheter device; and applying the global optimization algorithm to the variables to generate a catheter with optimized flow conditions.

2. The device of claim 1, wherein said variables further comprise:

velocity components, vorticity components, pressure, and/or concentration of blood and/or medium at specific locations of blood and/or medium inside and outside of the catheter device.

3. The device of claim 1, wherein said variables further comprise-shear stresses and/or vorticity components of the flow of the blood and/or medium inside and outside said catheter device.

4. The device of claim 3, wherein the specific location outside said catheter device being simulated is located in the vasculature or tubular body duct.

5. The device of claim 3, wherein said variables further comprise at least one of: Reynolds, Schmidt and/or Pulsating Flow parameters for the blood and/or medium.

6. The device of claim 1, wherein the global optimization algorithm further comprises applying constraints comprising at least one of:

a) maximum or minimum allowed sizes of the catheter and/or dimensions of said passages;

b) maximum allowed flow speeds and/or shear stresses;

c) maximum allowed pressure drop and skin friction;

e) maximum allowed medication concentration; and f) overall expected elapsed time needed for treatment.

7. The device of claim 1, wherein said global optimization algorithm comprises a genetic algorithm.

8. The device of claim 1, wherein said global optimization algorithm comprises at least one of simulated annealing, multistart and interval methods, continuous branch and bound methods, evolutionary algorithms, and tabu search and scatter search methods.

9. The device of claim 1, wherein the medium comprises at least one of agent, substance, material, thrombolytic agents, clot lysis agents, chemotherapies, cell slurries, gene therapy vectors, growth factors, contrast agents, angiogenesis factors, radionuclide slurries, anti-infection agents, anti-tumor compounds, and receptor-bound agents.

10. A method for delivering a medium to a lesion inside of a vascular structure or body duct by inserting a catheter device into a subject, said catheter device having a distal end and a proximal end, lumens there through, medium port holes, a blood inlet port, and a blood exit port, wherein said method comprises:

inflating an expandable component to block or impede the vascular flow of blood or other body fluid through the vasculature structure or the body duct;

delivering the medium through one of said lumens to said lesion through at least one of said medium port holes; and allowing blood of the vasculature of the subject to proximally enter through said blood inlet port and flow through one of said lumens and to exit on a side of said lesion toward said distal end of said catheter device through said blood exit port, wherein, a position of said inlet ports and said exit ports is determined by application of a global optimization algorithm comprising:

selecting variables including:
- a) geometrical shapes and dimensions of at least one of said lumens,
- b) relative locations and orientations of flow planes of at least one of said blood inlet port and said blood exit port, and
- c) concentration and residence time of the medium in the vicinity of a specific location outside said catheter device; and applying the global optimization algorithm to the variables to generate a catheter with optimized flow conditions.

11. The method of claim 10, wherein the medium comprises at least one of agent, substance, material, thrombolytic agents, clot lysis agents, chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic agent and/or diagnostic agent.

12. The method of claim 10, wherein said inflating comprises placing said expandable component on a side of said lesion that is toward said distal end of said catheter device or placing a portion of said expandable component on a side of said lesion that is toward said distal end of said catheter device.

13. The method of claim 10, wherein said inflating comprises placing said expandable component to surround said lesion or at least partially surround said lesion.

14. The method of claim 10, wherein said inflating comprises placing said expandable component adjacent to said lesion or at least partially adjacent to said lesion.

15. The method of claim 10, wherein said delivering the medium comprises sending the medium through said medium port holes that are located on a side of said expandable component that is toward said distal end of said catheter device, or partially located on a side of said expandable component that is toward said distal end of said catheter device.

16. The method of claim 10, wherein said delivering comprises:
sending said medium through said medium port holes that are located on a side of said expandable component that is toward said proximal end of said catheter device, or partially located on a side of said expandable component that is toward said proximal end of said catheter device; and
re-entering said medium through said medium port holes.

17. The method of claim 10, wherein:
said expandable component comprises an at least one port hole disposed thereto or in communication therewith; and
said delivering comprises sending said medium through said expandable component.

18. The method of claim 10, further comprising performing an angioplasty procedure on said lesion using said expandable component.

19. The method of claim 10, further comprising controlling the rate of irrigation of said medium with said lesion.

* * * * *